(12) United States Patent
Lee

(10) Patent No.: US 7,932,437 B2
(45) Date of Patent: Apr. 26, 2011

(54) DESIGNER PROTON-CHANNEL TRANSGENIC ALGAE FOR PHOTOBIOLOGICAL HYDROGEN PRODUCTION

(76) Inventor: James Weifu Lee, Knoxville, TN (US)

(*) Notice: Subject to any disclaimer, the term of this patent is extended or adjusted under 35 U.S.C. 154(b) by 617 days.

(21) Appl. No.: 11/748,531

(22) Filed: May 15, 2007

(65) Prior Publication Data

US 2007/0269864 A1 Nov. 22, 2007

Related U.S. Application Data

(60) Provisional application No. 60/800,952, filed on May 17, 2006.

(51) Int. Cl.
*C12N 15/82* (2006.01)
*C12N 1/12* (2006.01)
*C12N 1/20* (2006.01)

(52) U.S. Cl. ..................... 800/296; 435/257.2

(58) Field of Classification Search ........................ None
See application file for complete search history.

(56) References Cited

U.S. PATENT DOCUMENTS 6,989,252 B2 1/2006 Melis et al.
2005/0266541 A1 12/2005 Dillon

FOREIGN PATENT DOCUMENTS

WO WO2004093524 11/2004

OTHER PUBLICATIONS

Lee, J.W. et al. Applied Biochemistry and Biotechnology; 2003 vol. 105-108, pp. 303-313.*
Ghirardi M.L. et al. TIBTECH Dec. 2000; vol. 18 pp. 506-511.*
Chen, G. et al. The Journal of Biological Chemistry; vol. 268, No. 4; pp. 2363-2367.*
Patent Cooperation Treaty International Search Report (ISR) and Written Opinion (WO) mailed Jul. 31, 2008.
Nicholls, D. G., and S. J. Ferguson (1992) "The electron-transfer and light-capture pathway in green plants and algae," Bioenergetics 2, Chapter 6.4, pp. 169-182. Academic Press, New York.
Cinco, R. M., J. M. MacCinnis, and E. Greenbaum (1993) "The role of carbon dioxide in light-activated hydrogen production by *Chlamydomonas reinhardtii*," Photosynthesis Research, 38:27-33.
Buhrke, Thorsten, Oliver Lenz, Norbert Krauss, and Barbel Friedrich (2006) "Oxygen tolerance of the H2-sensing [NiFe] hydrogenase from *Ralstonia eutropha* H16, is based on limited access of oxygen to the active site," The Journal of Biological Chemistry, 280(25):23791-23796.
Lee, J. W., and E. Greenbaum (2003) "A new oxygen sensitivity and its potential application in photosynthetic H2 production," Applied Biochemistry and Biotechnology, vol. 105-108, p. 303-313.
Lee, J. W. and E. Greenbaum 1997. "A new perspective on hydrogen production by photosynthetic water splitting." ACS Symposium Series 666, Fuels and Chemicals from Biomass, B. C. Saha and J. Woodward, eds. Chapter 11, pp. 209-222.
Samuilov, V. D., E. L. Barsky, and A. V. Kitashov 1995. "ADRY agent-induced cyclic and non-cyclic electron transfer around photosystem II" Photosynthesis: from Light to Biosphere, P. Mathis (ed.), vol. II, 267-270. The Netherlands, Kluwer Academic Publishers.
Quinn, J. M., P. Barraco, M. Ericksson and S. Merchant (2000). "Coordinate copper- and oxygen-responsive Cyc6 and Cpx1 expression in Chlamydomonas is mediated by the same element." J Biol Chem 275: 6080-6089.
Teramoto, H., T. Ono and J. Minigawa (2001). "Identification of Lhcb gene family encoding the light-harvesting chlorophyll-a/b proteins of photosystem II in *Chlamydomonas reinhardtii*." Plant Cell Physiol 42(8): 849-856.
Lee, James W., Stephen L. Blankinship and Elias Greenbaum (1995). "Temperature effect on production of hydrogen and oxygen by *Chlamydomonas* cold strain CCMP1619 and wild type 137c," Applied Biochemistry and Biotechnology 51/52:379-386.
Lee, James W., Laurens Mets, and Elias Greenbaum (2002). "Improvement of photosynthetic efficiency at high light intensity through reduction of chlorophyll antenna size," Applied Biochemistry and Biotechnology, 98-100: 37-48.

* cited by examiner

*Primary Examiner* — Russell Kallis
(74) *Attorney, Agent, or Firm* — Knox Patents; Thomas A. Kulaga

(57) ABSTRACT

A designer proton-channel transgenic alga for photobiological hydrogen production that is specifically designed for production of molecular hydrogen ($H_2$) through photosynthetic water splitting. The designer transgenic alga includes proton-conductive channels that are expressed to produce such uncoupler proteins in an amount sufficient to increase the algal $H_2$ productivity. In one embodiment the designer proton-channel transgene is a nucleic acid construct (300) including a PCR forward primer (302), an externally inducible promoter (304), a transit targeting sequence (306), a designer proton-channel encoding sequence (308), a transcription and translation terminator (310), and a PCR reverse primer (312). In various embodiments, the designer proton-channel transgenic algae are used with a gas-separation system (500) and a gas-products-separation and utilization system (600) for photobiological $H_2$ production.

3 Claims, 5 Drawing Sheets

SEQUENCE LISTING

```
<160> NUMBER OF SEQ ID NOS: 3

<210> SEQ ID NO 1
<211> LENGTH: 945
<212> TYPE: DNA
<213> ORGANISM: Artificial Sequence
<220> FEATURE:
<223> OTHER INFORMATION: DNA construct with Plastocyanin transit-peptide
      DNA sequence

<400> SEQUENCE: 1
agaaaatctg gcaccacacc ataagggtca tagaatctag cgttatcctt ccacgagcgt        60
gtggcagcct gctggcgtgg acgagctgtc atgcgttgtt ccgttatgtg tcgtcaaacg       120
ccttcgagcg ctgcccggaa caatgcgtac tagtatagga gccatgaggc aagtgaacag       180
aagcgggctg actggtcaag gcgcacgata gggctgacga gcgtgctgac ggggtgtacc       240
```

```
gccgagtgtc cgctgcattc ccgccggatt gggaaatcgc gatggtcgcg cataggcaag      300
ctcgcaaatg ctgtcagctt atcttacatg aacacacaaa cactctcgca ggcactagcc      360
tcaaaccctc gaaacctttt tccaacagtt tacaccccaa ttcggacgcc gctccaagct      420
cgctccgttg ctccttcatc gcaccaccta ttatttctaa tatcgtagac gcgacaagat      480
gaaggctact ctgcgtgccc ccgcttcccg cgccagcgct gtgcgcccg tcgccagcct       540 gaaggccgct gctcagcgcg tggcctcggt cgccggtgtg tcggttgcct ctctggccct      600
gaccctggct gcccacgcca tggccggcat cggcgccgtg ctgaaggtcc tgaccaccgg      660
cctgcccgcc ctgatcagct ggatcaagcg caagcgccag cagtaaatgg aggcgctcgt      720
tgatctgagc cttgccccct gacgaacggc ggtggatgga agatactgct ctcaagtgct      780
gaagcggtag cttagctccc cgtttcgtgc tgatcagtct ttttcaacac gtaaaaagcg      840
gaggagtttt gcaattttgt tggttgtaac gatcctccgt tgattttggc ctctttctcc      900
atgggcgggc tgggcgtatt tgaagcggtt ctctcttctg ccgtt                      945

<210> SEQ ID NO 2
<211> LENGTH: 787
<212> TYPE: DNA
<213> ORGANISM: Artificial Sequence
<220> FEATURE:
<223> OTHER INFORMATION: DNA construct with Plastocyanin transit-peptide
      DNA sequence

<400> SEQUENCE: 2
agaaaatctg gcaccacacc gagctgtcat gcgttgttcc gttatgtgtc gtcaaacgcc       60
ttcgagcgct gcccggaaca atgcgtacta gtataggagc catgaggcaa gtgaacagaa      120
gcgggctgac tggtcaaggc gcacgatagg gctgacgagc gtgctgacgg ggtgtaccgc      180
cgagtgtccg ctgcattccc gccggattgg gaaatcgcga tggtcgcgca taggcaagct      240
cgcaaatgct gtcagcttat cttacatgaa cacacaaaca ctctcgcagg cactagcctc      300
aactcgagca tatgaaggct actctgcgtg cccccgcttc ccgcgccagc gctgtgcgcc      360
ccgtcgccag cctgaaggcc gctgctcagc gcgtggcctc ggtcgccggt gtgtcggttg      420
cctctctggc cctgaccctg gctgcccacg ccatggccgg catcggcgcc gtgctgaagg      480
tcctgaccac cggcctgccc gccctgatca gctggatcaa gcgcaagcgc cagcagtaat      540
ctagataaat ggaggcgctc gttgatctga gccttgcccc tgacgaacg gcggtggatg       600 gaagatactg ctctcaagtg ctgaagcggt agcttagctc ccgtttcgt gctgatcagt       660 cttttcaac acgtaaaaag cggaggagtt ttgcaatttt gttggttgta acgatcctcc       720
gttgattttg gcctctttct ccatgggcgg gctgggcgta tttgaagcgg ttctctcttc      780
tgccgtt                                                                787

<210> SEQ ID NO 3
<211> LENGTH: 972
<212> TYPE: DNA
<213> ORGANISM: Artificial Sequence
<220> FEATURE:
<223> OTHER INFORMATION: DNA construct with HydA1 transit peptide

<400> SEQUENCE: 3
agaaaatctg gcaccacacc ataagggtca tagaatctag cgttatcctt ccacgagcgt       60
gtggcagcct gctggcgtgg acgagctgtc atgcgttgtt ccgttatgtg tcgtcaaacg      120
ccttcgagcg ctgcccggaa caatgcgtac tagtatagga ccatgaggc aagtgaacag       180 aagcgggctg actggtcaag gcgcacgata gggctgacga gcgtgctgac ggggtgtacc      240
```

```
gccgagtgtc cgctgcattc ccgccggatt gggaaatcgc gatggtcgcg cataggcaag    300
ctcgcaaatg ctgtcagctt atcttacatg aacacacaaa cactctcgca ggcactagcc    360
tcaaaccctc gaaaccttt tccaacagtt tacaccccaa ttcggacgcc gctccaagct    420
cgctccgttg ctccttcatc gcaccaccta ttatttctaa tatcgtagac gcgacaagat    480
gtcggcgctc gtgctgaagc cctgcgcggc cgtgtctatt cgcggcagct cctgcagggc    540
gcggcaggtc gcccccgcg ctccgctcgc agccagcacc gtgcgtgtag cccttgcaac    600
acttgaggcg cccgcacgcc gcctaggcaa cgtcgcttgc gcggctatgg ccggcatcgg    660
cgccgtgctg aaggtcctga ccaccggcct gcccgccctg atcagctgga tcaagcgcaa    720
gcgccagcag taaatggagg cgctcgttga tctgagcctt gcccctgac gaacggcggt    780 ggatggaaga tactgctctc aagtgctgaa gcggtagctt agctccccgt ttcgtgctga    840
tcagtctttt tcaacacgta aaaagcggag gagttttgca attttgttgg ttgtaacgat    900
cctccgttga ttttggcctc tttctccatg ggcgggctgg gcgtatttga agcggttctc    960
tcttctgccg tt                                                        972
```

US 7,932,437 B2

DESIGNER PROTON-CHANNEL TRANSGENIC ALGAE FOR PHOTOBIOLOGICAL HYDROGEN PRODUCTION

CROSS-REFERENCE TO RELATED APPLICATIONS

This Application claims the benefit of U.S. Provisional Application No. 60/800,952, filed on May 17, 2006.

STATEMENT REGARDING FEDERALLY SPONSORED RESEARCH OR DEVELOPMENT

This invention was made with Government support under Contract No. DE-AC05-00OR22725 awarded by the United States Department of Energy. The Government has certain rights in this invention.

BACKGROUND OF THE INVENTION

1. Field of Invention

This invention pertains to a designer photosynthetic organism that is specifically designed for production of molecular hydrogen ($H_2$) through photosynthetic water splitting. The various embodiments include (1) targeted genetic insertion of a proton channel into algal thylakoid membrane and (2) novel application of an anaerobic promoter such as a hydrogenase promoter to act as a genetic switch in controlling the expression of a designer proton channel gene. In particular, this invention pertains to a proton-channel designer alga for enhanced photobiological $H_2$ production. Various embodiments solve the following four major problems that currently challenge those in the field of photobiological $H_2$ production: (1) restriction of photosynthetic $H_2$ production by accumulation of a proton gradient, (2) competitive inhibition of photosynthetic $H_2$ production by $CO_2$, (3) requirement of bicarbonate binding at photosystem II (PSII) for efficient photosynthetic activity, and (4) competitive drainage of electrons by $O_2$ in algal $H_2$ production. The application titled "Switchable photosystem-II designer algae for photobiological hydrogen production" and filed on the same day and by the same inventor as this application is hereby incorporated by reference in its entirety.

2. Background

Algal (such as *Chlamydomonas reinhardtii*, *Platymonas subcordiformis*, *Chlorella fusca*, *Ankistrodesmus braunii*, and *Scenedesmus obliquus*) photosynthetic hydrogen ($H_2$) production from water has tremendous potential to be a clean and renewable energy resource. However, there are a number of technical issues that must be addressed before algal $H_2$ production can become practical. Currently, there are four proton-gradient-associated physiological problems that challenge researchers and investors in the field of photobiological $H_2$ production are: (1) restriction of photosynthetic $H_2$ production by accumulation of a proton gradient, (2) competitive inhibition of photosynthetic $H_2$ production by $CO_2$, (3) requirement of bicarbonate binding at photosystem II (PSII) for efficient photosynthetic activity, and (4) competitive drainage of electrons by $O_2$ in algal $H_2$ production. In order for the photobiological $H_2$-production technology to work efficiently, all of these four problems must be solved. The various embodiments teach how to generate a switchable proton-channel designer alga to solve these four physiological problems for enhanced photobiological $H_2$ production from water. The following describes the four physiological problems that are solved by various embodiments:

(1). Restriction of photosynthetic $H_2$ production by accumulation of a proton gradient across algal thylakoid membrane. As illustrated in FIG. 1, for each $H_2$ molecule produced photosynthetically, six protons are translocated across the algal thylakoid membrane: two protons are generated by photosystem II (PSII) water splitting at the lumen side and consumed by ferredoxin (Fd)/hydrogenase-catalyzed production of $H_2$ by reduction of protons in the stroma; two protons per pair of electrons flowing from $Q_B$ site to photosystem I (PSI) are physically taken from the stroma by the reduction of plastoquinone (PQ) to $PQH_2$ at $Q_B$ site and then released into the lumen with oxidation of $PQH_2$ at the $Q_o$ site of the cytochrome b/f (Cyt b/f) complex; and two protons per pair of electrons are transported from the stroma into the lumen by the Q-cycle around the Cyt b/f complex. Since the thylakoid membrane has limited permeability to protons, photosynthetic electron transport will result in accumulation of protons inside the lumen of the thylakoids. In photosynthetic $CO_2$ fixation, this proton gradient across the thylakoid membrane is used by the coupling factor $CF_oCF_1$ complex to drive the formation of ATP that is required by the Calvin cycle. However, unlike the Calvin cycle, the Fd/hydrogenase $H_2$ production pathway does not consume ATP. Consequently, under the conditions of $H_2$ photoevolution where the consumption of ATP by the Calvin cycle stops due to the absence of $CO_2$, the $CF_oCF_1$-mediated conduction of protons from the lumen to the stroma will quickly become limiting because of the accumulation of ATP and the shutdown of ATP synthase activity. As a result, photosynthetic $H_2$ production quickly results in an increased proton gradient across the thylakoid membrane that has no mechanism for dissipation. The static back-proton gradient seriously impedes the electron transport, thus limiting the rate of $H_2$ production, since electron transport from water through PSII, PQ, Cyt b/f, PC, and PSI to the Fd/hydrogenase pathway is coupled with proton translocation across the thylakoid membrane (FIG. 1). This is one of the reasons that photosynthetic $H_2$ production is saturated at a much lower light intensity than that of photosynthetic $CO_2$ fixation.

(2). Competitive inhibition of photosynthetic $H_2$ production by $CO_2$. As illustrated in FIG. 1, $CO_2$ fixation by the Calvin cycle can compete with the Fd/hydrogenase pathway for photosynthetically generated electrons, resulting in competitive inhibition of $H_2$ production. This inhibition of $H_2$ evolution by $CO_2$ has been characterized in experimental studies at ORNL. The result showed that the algal system is sensitive to $CO_2$ at a concentration as low as 30 ppm. Steady-state $H_2$ photoevolution was inhibited to nearly zero by injection of 58 ppm $CO_2$. Therefore, unless the alga is genetically reengineered to control the Calvin cycle activity, photosynthetic $H_2$ production would require a nearly $CO_2$-free environment.

(3). Requirement for bicarbonate binding at PSII for efficient photosynthetic activity. Bicarbonate ($HCO_3^-$) is believed to be an activator of PSII. Experimental studies have demonstrated that addition of $HCO_3^-$ to $HCO_3^-$-depleted samples can result in a 6- to 7-fold stimulation of PSII electron-transport activity. Because $CO_2$ and $HCO_3^-$ are interchangeable in aqueous medium, removal of $CO_2$ can lead to depletion of $HCO_3^-$, thus affecting PSII activity. This presents a dilemma when one tries to reduce the $CO_2$ concentration as required to limit the competitive inhibition of $H_2$ production by $CO_2$.

(4). Competitive drainage of electrons by $O_2$ in algal $H_2$ production. We have recently discovered a new $O_2$ sensitivity in algal $H_2$ production that is distinct from the $O_2$ sensitivity of hydrogenase per se. This $O_2$ sensitivity is apparently linked to the photosynthetic $H_2$ production pathway that is coupled to proton translocation across the thylakoid membrane. Addition of the proton uncoupler FCCP eliminates this mode of $O_2$ inhibition on $H_2$ photoevolution. This inhibition is likely due to the background $O_2$, which apparently serves as a terminal electron acceptor in competition with the $H_2$-production pathway for photosynthetically generated electrons from water splitting. The Rubisco enzyme of the Calvin cycle is known to be also an oxygenase in addition to its carboxylase activity. Therefore, as illustrated in FIG. 1, $O_2$ could act as an electron acceptor through Rubisco at the Calvin cycle with the mechanism known as the photorespiration in competition with the Fd/hydrogenase $H_2$ production pathway for the photosynthetically generated electrons from water. That is, the drainage of electrons by $O_2$ is likely to occur at the point of Rubisco, which is one of the key enzymes of the Calvin cycle. This competitive inhibition of $H_2$ production by $O_2$ is much more of a problem than the traditionally known $O_2$ sensitivity of the hydrogenase per se. Our experimental studies demonstrated that photosynthetic $H_2$ production can be inhibited by an $O_2$ concentration as low as about 500-1000 ppm while the algal hydrogenase is still active at an $O_2$ concentration as high as 5000 ppm. The competitive inhibition of $H_2$ production by $O_2$ is about 10 times more sensitive to $O_2$ than the traditionally known $O_2$ sensitivity of hydrogenase. The drainage of electrons by $O_2$ in competition with the Fd/hydrogenase $H_2$ production pathway is 10 time more sensitive to $O_2$ than the $O_2$ sensitivity of the hydrogenase. Therefore, this is also a serious problem that must be solved in order for the photobiological $H_2$ production technology to work efficiently.

Many of the approaches reported in the field of studies such as the "sulfur-deprivation"-based approach do not solve any of these four major physiological problems that seriously limit the energy efficient and the rate (yield) of algal $H_2$ production. The solar-to-hydrogen energy conversion efficiency of the available algal $H_2$-production technologies including the "sulfur-deprivation"-based approach is typically only less than 0.1%, which is not practical for commercial use. The reason why the solar-to-hydrogen energy conversion efficiency of the photobiological $H_2$-production process is so poor is because the four major physiological problems in algal $H_2$ production described above had not been solved by any of the prior arts in this field. The various embodiments uniquely solve all of these four major problems in algal $H_2$ production through creation of a designer proton-channel transgenic alga with a systematic approach, which improves the solar-to-hydrogen energy conversion efficiency by a factor of more than 10 times in the field of renewable photobiological hydrogen production from water.

The various embodiments are based on new scientific understanding that all of these four problems are somehow associated with the proton gradient across the algal thylakoid membrane in relation to photobiological $H_2$ production. Therefore, it is possible to solve all of these four problems by use of a proton shuttling mechanism such as a proton channel across algal thylakoid membrane. By testing the effect of proton uncouplers such as trifluoromethoxy carbonylcyanide phenylhydrazone (FCCP) in algal $H_2$ production, the inventor recently accomplished some new and preliminary understanding that use of proton uncoupler FCCP with a function similar to a proton channel in the thylakoid membrane eliminates both the problem of back-proton accumulation and the newly discovered $O_2$ sensitivity. See, "A new perspective on hydrogen production by photosynthetic water splitting," by Lee, J. W. and E. Greenbaum, ACS Symposium Series 666, *Fuels and Chemicals from Biomass*, B. C. Saha and J. Woodward, eds., Chapter 11, pp. 209-222, 1997; "A new oxygen sensitivity and its potential application in photosynthetic $H_2$ production," by Lee, J. W., and E. Greenbaum, *Applied Biochemistry and Biotechnology*, Vol. 105-108, pg 303-313, 2003. As demonstrated by the experimental results shown in FIG. 2, addition of 5 µM FCCP produced a dramatic reversal of $O_2$ inhibition on $H_2$ photoevolution. The rate of $H_2$ production rose to about 16 µmol $H_2$/mg Chl.h. This FCCP-stimulated $H_2$ production is clearly photodependent. As soon as the actinic light was turned off, the $H_2$ production stopped. However, most of these chemical proton uncouplers—such as FCCP, carbonyl cyanide m-chlorophenylhydrazone (CCCP), and anilinothiophene—have undesirable side effects, including the acceleration of the deactivation of the water-splitting system Y (ADRY) effect, which can damage the photosynthetic activity in algal cells. See, "ADRY agent-induced cyclic and non-cyclic electron transfer around photosystem II," by Samuilov, V. D., E. L. Barsky, and A. V. Kitashov, Photosynthesis: from Light to Biosphere, P. Mathis (ed.), Vol. II, 267-270, 1995. As shown in FIG. 2, the FCCP-enhanced photoevolution of $H_2$ can last for more than 4 hours with some decay. This decay is due to the ADRY effect, in which FCCP gradually inhibits photosystem II (PSII) activity by deactivation of the photosynthetic water-splitting complex in the $S_2$ and $S_3$ states. Furthermore, those chemical uncouplers (such as FCCP) are hazardous materials that are environmentally unacceptable for large-scale applications. These challenges and scientific understandings indicate the need of finding a new solution with a polypeptide proton channel that does not have the ADRY effect to solve the four proton-gradient related problems in photobiological $H_2$ production. Consequently, the various embodiments are created with new knowledge and scientific progresses to overcome the roadblocks including the four proton-gradient related problems to photosynthetic $H_2$ production from water.

BRIEF SUMMARY OF THE INVENTION

In accordance with various embodiments, there are provided designer transgenic algae comprising proton-conductive channels that are expressed to produce such uncoupler proteins in an amount sufficient to increase the algal $H_2$ productivity, relative to non-transgenic algae of the same species. The DNA construct that represents a designer proton-channel gene includes, in one embodiment, an externally inducible promoter, a photosynthetic membrane-targeting sequence, a proton-channel encoding sequence, a transcription and translation terminator, and a pair of polymerase chain reaction (PCR) primers. The designer proton-channel transgenic algae are created by genetic transfer of a designer proton-channel DNA construct into a host alga selected from a group comprising green algae, brown algae, red algae, blue-green algae, marine algae, freshwater algae, cold-tolerant algal strains, heat-tolerant algal strains, oxygen-tolerant-hydrogenase algal strains, $H_2$-consuming-activity-deleted algal strains, uptake-hydrogenase-deleted algal strains, and combinations thereof. Various embodiments solve the following four major problems that currently challenge those in the field of photobiological $H_2$ production: (1) restriction of photosynthetic $H_2$ production by accumulation of a proton gradient, (2) competitive inhibition of photosynthetic $H_2$ production by $CO_2$, (3) requirement of bicarbonate binding at photosystem II (PSII) for efficient photosynthetic activity, and (4) competitive drainage of electrons by $O_2$ in algal $H_2$ production.

Therefore, the designer proton-channel transgenic algae are useful to photobiologically produce $H_2$ from water using solar energy. Examples of the designer proton-channel nucleic acid constructs are also provided that are useful in methods for producing the transgenic algae. Additional specialized features such as the tolerances to cold and/or hot environments and the capabilities of using freshwater and/or seawater are also incorporated into the designer proton-channel algae.

The various embodiments teach how the designer proton-channel transgenic algae may be used with bioreactor systems and gas-products-separation-utilization for photobiological $H_2$ production. There are a number of ways that the designer proton-channel algae can be used for photobiological $H_2$ production. First, the designer algae can be used with a suitable photo-bioreactor and gas-product separation and utilization system for simultaneous photosynthetic production of $H_2$ and $O_2$ from water. In one embodiment, to obtain maximal benefit, it is a preferred practice to grow the designer algae photoautotrophically using air $CO_2$ as the carbon source under the aerobic conditions in a minimal medium that contain the essential inorganic nutrients, which can be readily supplied by adding relatively small amounts of fertilizers and mineral salts into the liquid medium. Before the designer proton channels are expressed and inserted into their photosynthetic thylakoid membrane, no organic substrate such as acetate is required to grow the designer algae. That is, large amounts of biocatalysts (designer algae) can be inexpensively grown in a short period of time because, under aerobic conditions such as in an open pond, the designer algae can autotrophically grow by themselves using air $CO_2$ as rapidly as their wild-type parental strains. This feature can provide a cost-effective solution for generating large amounts of photoactive catalysts (the designer proton-channel algae) for renewable $H_2$ production. When the algal culture is grown and ready for $H_2$ production, the algal cells (culture) is placed under anaerobic conditions to express the designer proton-channel gene simultaneously with the induction of the hydrogenase enzyme, thus turning the algal cells into efficient and robust "green machines" that are perfect for photoevolution of $H_2$ and $O_2$ by water splitting. Use of a gas-separation-utilization system including a coupled fuel-cell operation that consumes the gas products $H_2$ and $O_2$ for electricity generation effectively removes the gas products from the algal reactor to maintain a relatively low partial pressure of $H_2$ and $O_2$ in the bioreactor in favor of continued production of $H_2$ and $O_2$ by photosynthetic water splitting.

The various embodiments further teach how to use the designer proton-channel algae in combination of certain $O_2$-consuming microbes such as facultative $H_2$-producing bacteria to produce pure $H_2$ and $CO_2$ from $H_2O$ and organic substrates such as acetate, ethanol, carbohydrates, lipids, and proteins. In this case, the designer proton-channel algae produce $H_2$ and $O_2$ by photosynthetic water splitting while the $O_2$-consuming microbes then use organic substrates to effectively consume the $O_2$ molecules that are generated by the algae. As a result, the bioreactor remains anaerobic in favor of continued photosynthetic $H_2$ production. The net process is the conversion of $H_2O$ and organic substrate to pure $H_2$ and $CO_2$. Since the gas products in this case are essentially pure $H_2$ and $CO_2$ without $O_2$, the technical problems associated with the $H_2$ and $O_2$ mixture, including the potential inhibition of hydrogenase by the generated $O_2$ molecules and the $H_2$ and $O_2$ gas-separation and safety issues, are avoided. The separation of $H_2$ from $CO_2$ is readily accomplished. The $H_2$ gas produced by this process can be used also for fuel-cell operation to generate electricity and/or for cash sales as a valuable chemical stock or hydrogen fuel.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

Figure 1:
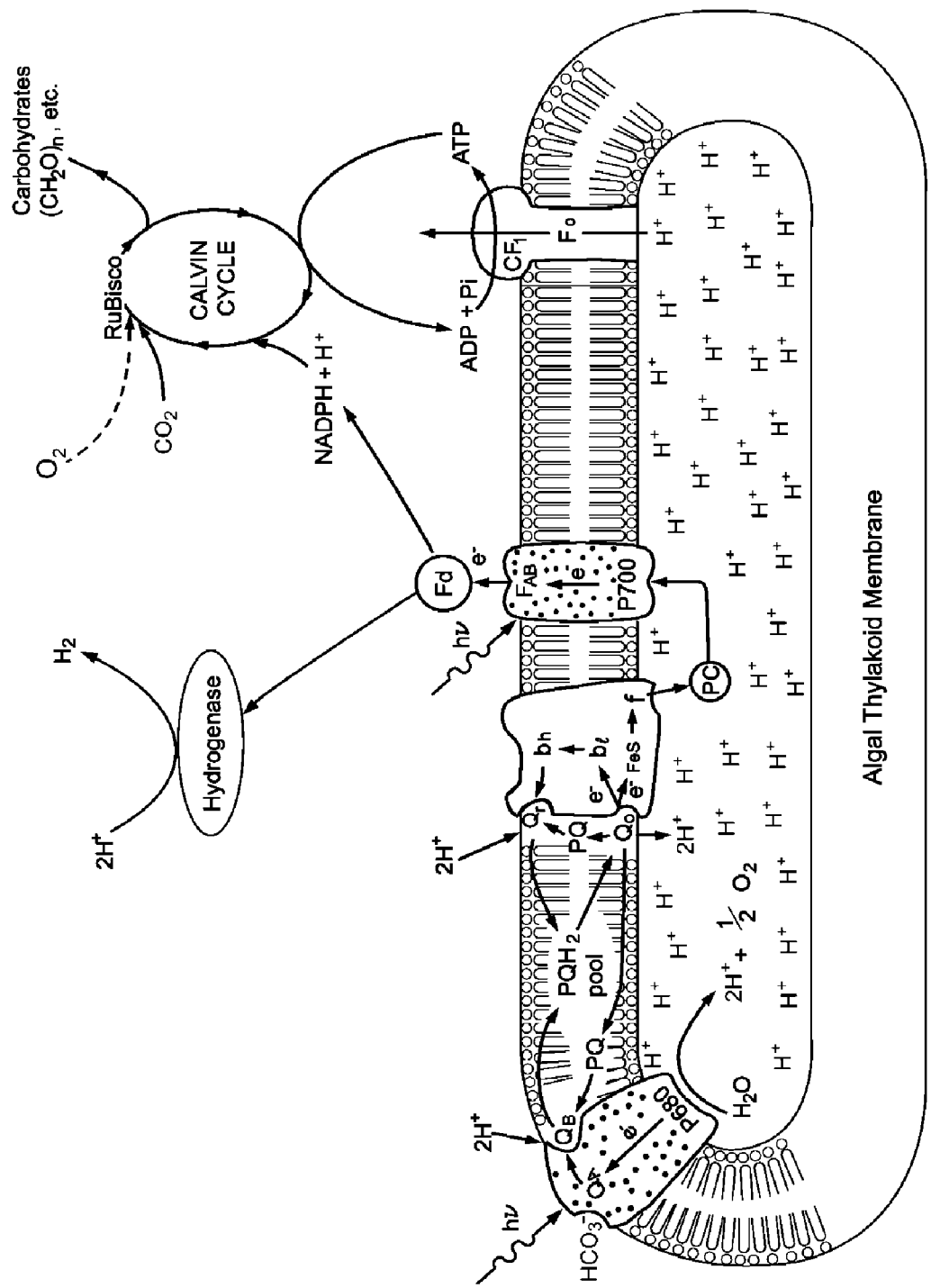
FIG. 1 illustrates the four proton-gradient-related physiological problems of the photosynthetic hydrogen ($H_2$) production pathway in wild-type algae such as Chlamydomonas reinhardtii.
Figure 2:
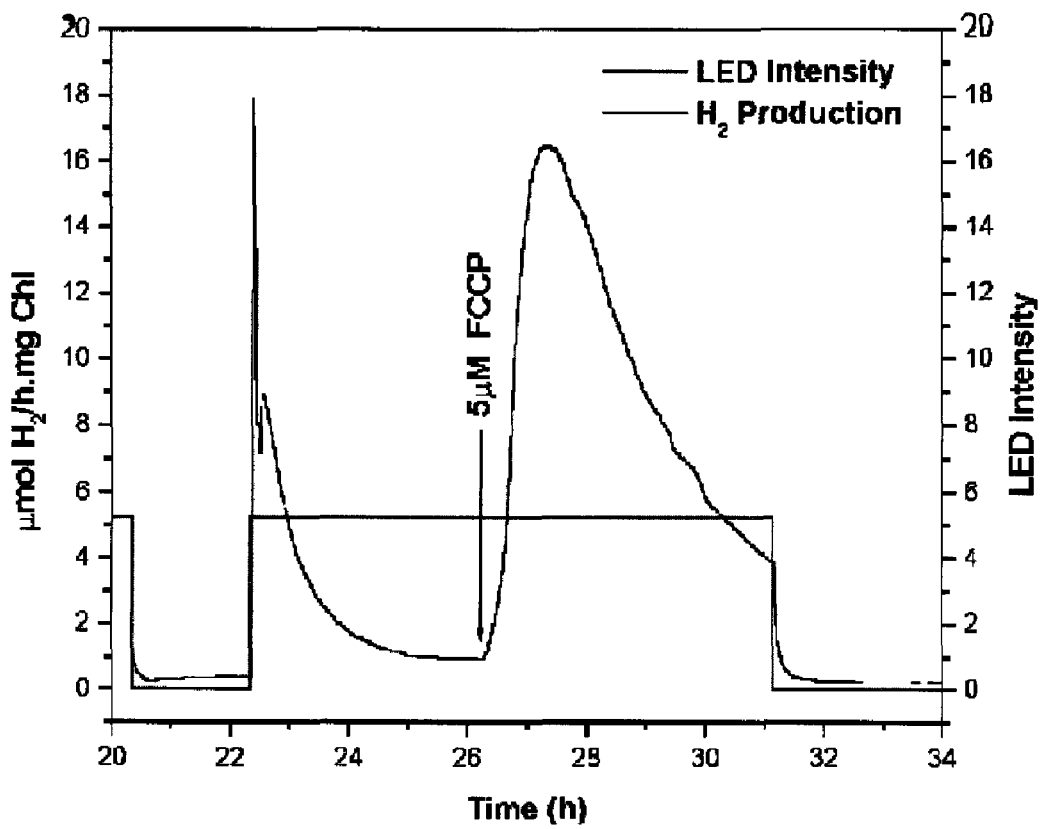
FIG. 2 presents proof-of-principle experimental data that demonstrate significant stimulation of photosynthetic $H_2$ production in wild-type alga Chlamydomonas reinhardtii 137c following addition of the proton uncoupler FCCP in a background atmosphere of 1000-ppm $O_2$.

In accordance with various embodiments, there are provided transgenic designer algae comprising switchable transgenes wherein each transgene encodes for a proton-conductive channel in the algal photosynthetic thylakoid membrane for enhanced photobiological $H_2$ production.

In one embodiment, the programmable genetic insertion of proton channels into algal thylakoid membrane is achieved by transformation of a host alga with a DNA construct 300 (illustrated in FIG. 3) that contains a designer polypeptide proton-channel gene linked with an externally inducible promoter such as a redox-condition-sensitive hydrogenase promoter serving as a genetic switch. As shown in the embodiment illustrated in FIG. 3, the designer proton-channel transgene is a nucleic acid construct 300 comprising: a) a PCR forward primer 302; b) an externally inducible promoter 304; c) a transit targeting sequence 306; d) a designer proton-channel encoding sequence 308; e) a transcription and translation terminator 310; and f) a PCR reverse primer 312.

In accordance with various embodiments, any of the components a) through f) 302, 304, 306, 308, 310, 312 of this DNA construct 300 are adjusted to suit for certain specific conditions. In practice, any of the components a) through f) 302, 304, 306, 308, 310, 312 of this DNA construct 300 are applied in full or in part, and/or in any adjusted combination to achieve more desirable results.

Figure 4A:
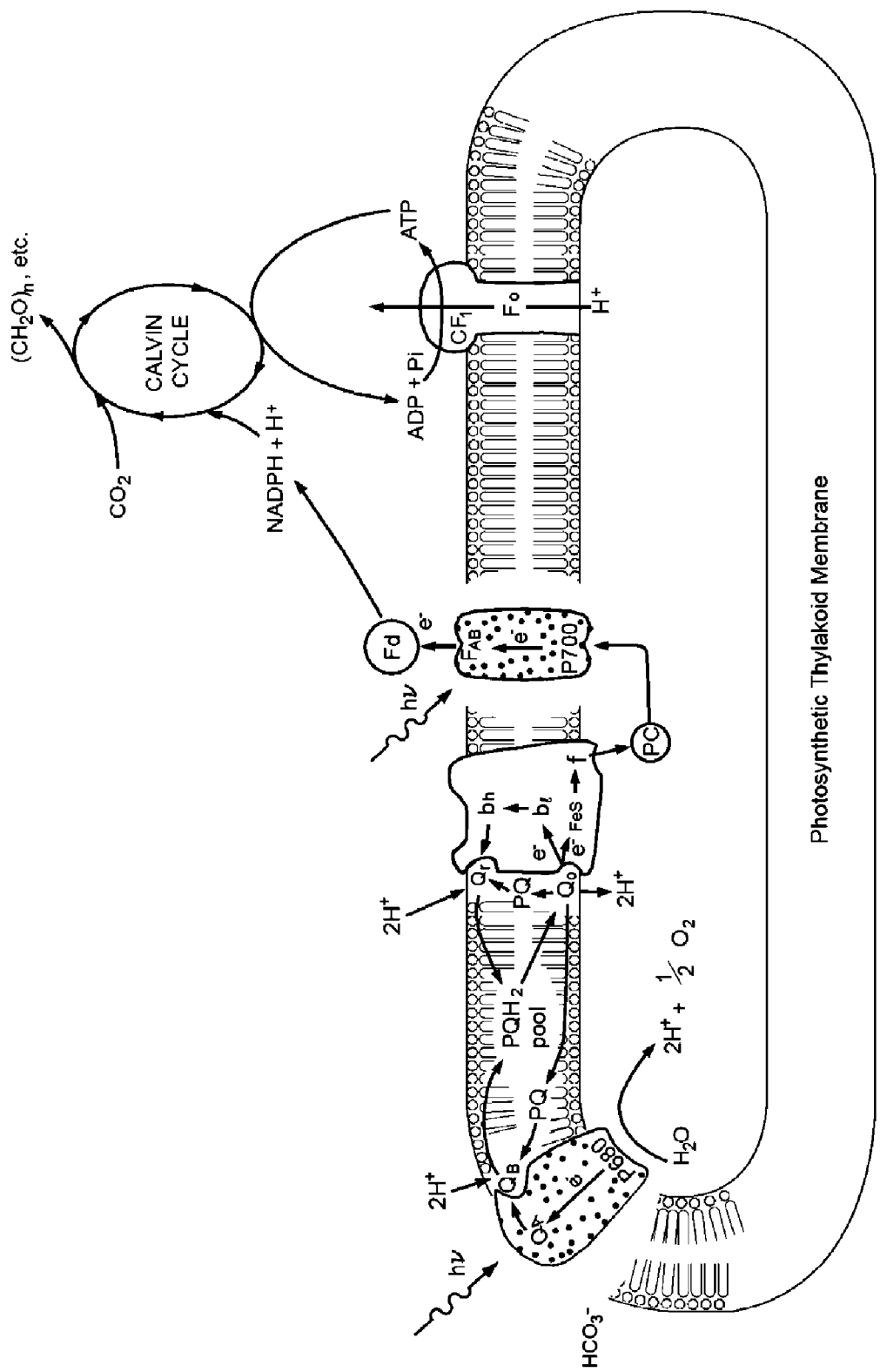
FIG. 4A shows one embodiment of a designer proton-channel alga performing autotrophic photosynthesis using ambient-air $CO_2$ as the carbon source and growing normally under aerobic conditions.
Figure 4B:
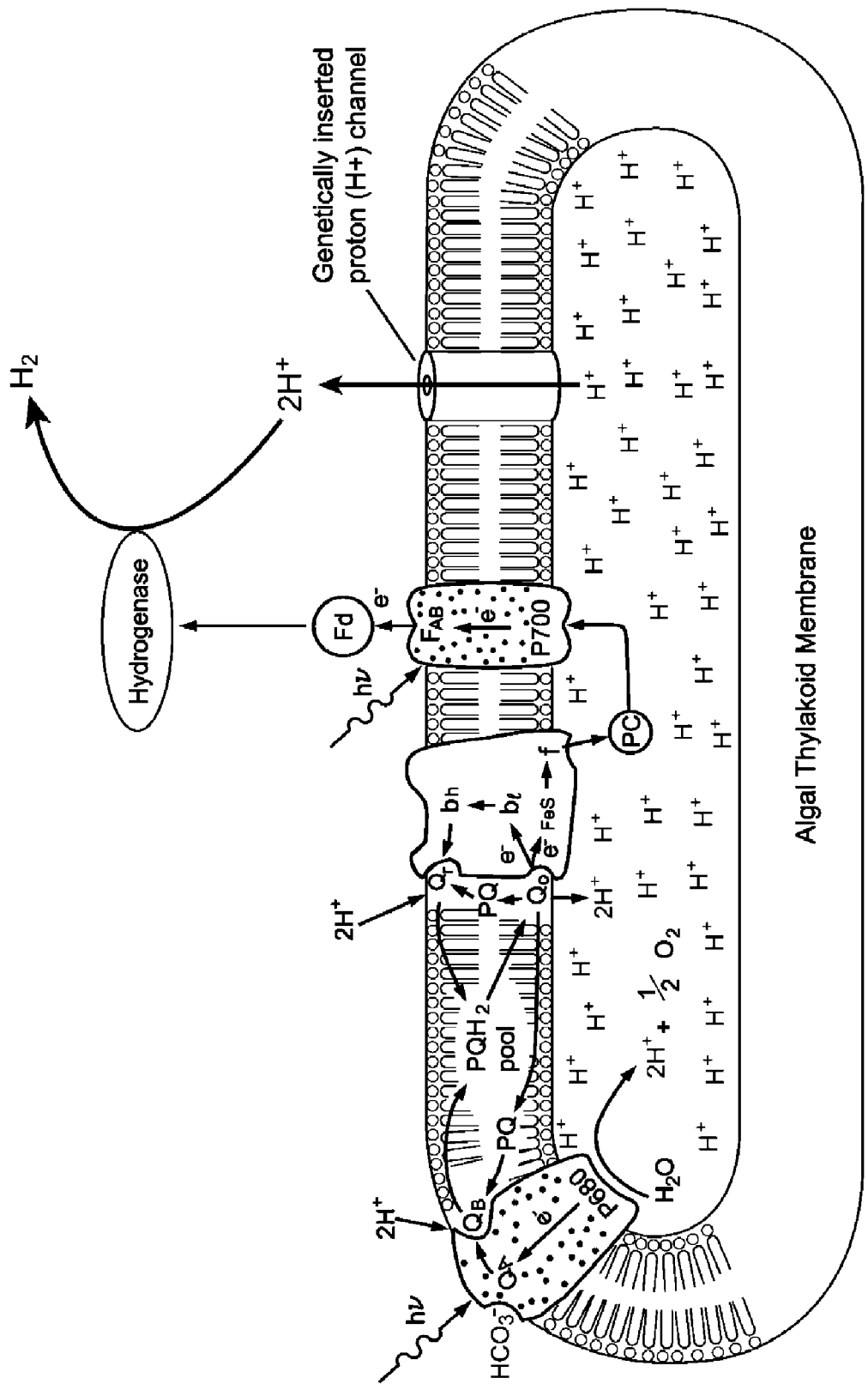
FIG. 4B shows another embodiment of a designer proton-channel alga when a designer proton-channel is expressed/inserted into the algal photosynthetic thylakoid membrane upon induction of the hydrogenase under $H_2$-producing conditions including (but not limited to) anaerobic conditions.

As illustrated in FIG. 4A, the proton-channel designer alga performs autotrophic photosynthesis using ambient-air $CO_2$ as the carbon source and grows normally under aerobic conditions, such as in an open pond. When the algal culture is grown and ready for $H_2$ production, the designer proton-channel transgene will then be expressed simultaneously with the induction of the hydrogenase enzyme under anaerobic conditions because of the use of the hydrogenase promoter. The expression of the proton-channel gene produces polypeptide proton channels in the algal thylakoid membrane for enhanced photobiological $H_2$ production (FIG. 4B). The designer proton channel is a trans-membrane biopolymer that contains a proton conductive path or channel that allows protons to freely pass through. According to the illustrated embodiment, the controllable expression of the proton-channel gene triggers a series of related events for enhanced $H_2$ production in the proton-channel designer alga. First, the expression of the proton-channel gene produces polypeptide proton channels in the thylakoid membrane, thus dissipating the proton gradient across the membrane without ATP formation. Therefore, problem 1 (Proton accumulation in algal thylakoids) is eliminated. Second, because the designer proton channel can allow protons to pass through without making ATP, the cessation of photophosphorylation (ATP formation) caused by action of the proton channels can, in turn, switch off the Calvin-cycle activity ($CO_2$ fixation), which requires ATP and competes with the Fd/hydrogenase $H_2$-production pathway for the photosynthetically generated electrons. As a result, the competitive inhibition of $H_2$ production by $CO_2$ (problem 2) is now eliminated and photosynthetic $H_2$ production in the designer alga occurs in the presence of $CO_2$. That is, when the Calvin-cycle activity which represents a collection of enzymes including Rubisco is inactivated, $CO_2$ is no longer able to act as a terminal electron acceptor in competition with the Fd/hydrogenase $H_2$-production pathway. Since photosynthetic $H_2$ production in the proton-channel-expressed designer alga no longer requires a $CO_2$ ($HCO_3^-$)-free environment, the requirement for $HCO_3^-$ binding at photosystem II (PSII) for efficient photosynthetic activity (problem 3) is also no longer an issue. The requirement is satisfied in the designer alga by leaving some $CO_2$ in the medium to form the needed bicarbonate ($HCO_3^-$) so that PSII activities including PSII photochemical charge separation, electron transfer, water-splitting, and oxygen generation become more efficient and stable. Finally, because the drainage of electrons by $O_2$ (problem 4) at the point of Rubisco which also competes with the $H_2$-production pathway for photosynthetically generated electrons is also proton-gradient dependent, this problem is also avoided by the dissipation of the proton gradient with the expression of the designer proton channel. This makes sense because when the Calvin-cycle activity including Rubisco and its oxygenase activity is inactivated by the action of the proton channel, $O_2$ will also no longer be able to act as a terminal electron acceptor there.

Therefore, all the four proton gradient-related physiological problems are solved through the use of the illustrated embodiment. The co-expression of the polypeptide proton channel and hydrogenase genes make this alga a more efficient and robust system for production of $H_2$ and $O_2$ by photosynthetic water splitting. This organism contains normal mitochondria, which can use the reducing power (NADH) from organic reserves and/or exogenous substrates such as acetate, ethanol, carbohydrate, lipid, amino acids and protein to power the cell immediately after its return to aerobic conditions. Therefore, when the algal cell is returned to aerobic conditions after its use under anaerobic conditions for photoevolution of $H_2$ and $O_2$, the cell stops generating polypeptide proton channels in thylakoid membranes and starts to restore its normal photoautotrophic capability by synthesizing functional thylakoids. Consequently, it is possible to use this type of genetically transformed organism for repeated cycles of photoautotrophic culture growth under normal aerobic conditions (FIG. 4A) and efficient production of $H_2$ and $O_2$ by photosynthetic water splitting under anaerobic conditions (FIG. 4B). Proper application enhances photobiological $H_2$ productivity by a factor of more than 10 times by eliminating the four proton-gradient-associated problems.

According to one embodiment, a proton channel suitable for this application to enhance photobiological $H_2$ production is a proton-conductive polypeptide or protein structure that is genetically encoded but has no undesirable or harmful side-effects. The passage of protons through a proton-conductive polypeptide or protein structure is achieved, in various embodiments, by using a number of proton-conduction mechanisms that include (but are not limited to): 1) direct transport through a nanometer pore of a polypeptide or protein structure that contains or creates such a proton-conductive pore typically in the pore size range of 0.2-10 nm in algal photosynthetic membranes; and 2) conduction by a proton-conductive wire of a polypeptide or protein structure that contains or creates such a proton-conductive path, which does not necessarily require a physical pore.

Examples of proton-conductive polypeptide or protein structures that can be used and/or modified for this application are the structures of melittin, gramicidin, $CF_o$ protein (the proton channel of chloroplast coupling factor $CF_oCF_1$), $F_o$ protein (the proton-channel structure of mitochondrial coupling factor $F_oF_1$), and their analogs including artificially designed polypeptide proton channels. That is, the molecular structure (and thus the DNA sequence) of a polypeptide proton channel can be designed according to these natural proton-channel structures and their analogs at a nanometer scale.

Another aspect is the innovative application of an externally inducible promoter such as a hydrogenase promoter. To function as intended, the designer proton-channel protein is inducibly expressed under hydrogen-producing conditions such as under anaerobic conditions. An algal hydrogenase promoter, such as the promoter of the hydrogenase gene (Hyd1) of *Chlamydomonas reinhardtii*, can be used as an effective genetic switch to control the expression of the proton channel gene to the exact time and conditions where it is needed for $H_2$ production. That is, the proton channels are synthesized only at the time when the hydrogenase is induced and ready for $H_2$ production under anaerobic conditions. Therefore, the hydrogenase promoter is employed as an inducible promoter for the DNA construct 300 to serve as a genetic switch to control the expression of the designer polypeptide proton-channel gene. The reason that the designer alga can perform autotrophic photosynthesis using $CO_2$ as the carbon source under aerobic condition is because the designer proton-channel gene is not expressed under aerobic conditions owning to the use of a hydrogenase promoter as a genetic switch, which can be turned on only under the anaerobic conditions when needed for photobiological $H_2$ production.

In addition to the hydrogenase promoter, in various embodiments other promoters are used to construct the desired genetic switch for designer proton-channel gene. *Chlamydomonas* cells contain several nuclear genes that are coordinately induced under anaerobic conditions. These include the hydrogenase structural gene itself (Hyd1), the Cyc6 gene encoding the apoprotein of Cytochrome $C_6$, and the Cpx1 gene encoding coprogen oxidase. The regulatory regions for the latter two have been well characterized, and a region of ~100 bp proves sufficient to confer regulation by anaerobiosis in synthetic gene constructs. The promoter strengths of these three genes vary considerably; each may thus be selected to control the level of the designer proton-channel expression for enhanced photobiological production of $H_2$. There are a number of other regulated promoters that can also be used and/or modified to serve as the genetic switches. For example, the nitrate reductase (Nia1) promoter which is induced by growth in nitrate medium and repressed in nitrate-deficient but ammonium-containing medium is used to control the expression of the designer genes according to the concentration levels of nitrate in a culture medium as well. Therefore, inducible promoters that are used and/or modified in various embodiments to serve this purpose includes, but are not limited to, hydrogenase promoters, Cytochrome $C_6$ (Cyc6) promoter, Nia1 promoter, CabII-1 promoter, Ca1 promoter, Ca2 promoter, coprogen oxidase promoter, and/or their analogs and modified designer sequences. In various embodiments, use of these externally inducible promoters creates varieties of designer algae.

Another aspect is the targeted insertion of the designer proton channels into algal photosynthetic membrane or into both the photosynthetic membrane and other cellular membranes including the mitochondria and/or plasma membranes to suit for the specific applications. For example, in the case of green algae including *Chlamydomonas*, when recyclable growth of the designer algae culture is desired, it is best to insert the proton channels only into the algal thylakoid membrane, exactly where the action of proton channels is needed to enhance $H_2$ production. If expressed without a targeted insertion mechanism, the polypeptide proton channels might be inserted nonspecifically into other membrane systems including the mitochondria and plasma membranes in addition to the thylakoid membranes. Although an expression of the proton channel gene in such a nonspecific manner could still transform an algal cell into a more efficient and robust photosynthetic apparatus for $H_2$ production, other cellular functions such as the respiratory process would probably be disabled because of the potential effect of the proton channels that are nonspecifically inserted into other organelles such as the mitochondria. As a result, this type of algal cells with insertion of the proton channels into both the photosynthetic membrane and other cellular membranes, such as the mitochondrial membranes, can still be used for enhanced $H_2$ production, but the cells would probably no longer be able to grow or regenerate themselves after the expression of the designer proton channels is turned on. That is, when the expression of the designer proton channels is turned on in this type of non-regenerative proton-channel designer algae, the algal culture will become dedicated "green machine" materials for enhanced $H_2$ production and the cells will no longer be able to grow even if they are returned to aerobic condition because the other cellular functions such as the function of the mitochondria are all impaired by the insertion of proton channels. This non-regenerative feature provides a benefit: help ensure biosafety in using the genetically modified algae. This is because after the designer proton channels are inserted into both the photosynthetic membrane and the mitochondrial membranes, the designer algal cells become dedicated non-living "green machine" materials for enhanced $H_2$ production, but without any potential risks of sexually passing any of their genes to any other cells. In various embodiments, the non-regenerative feature is achieved by use of two designer proton-channel genes: one with a mitochondrial targeting sequence to insert proton channels into the algal mitochondrial membrane and one with a thylakoid targeting sequence to insert proton channels into the algal thylakoid membrane. When the two designer proton-channel genes are both expressed, the designer cells immediately become dedicated non-living "green machine" materials for enhanced $H_2$ production. Therefore, in one embodiment, it is a preferred practice to keep growing this type of non-regenerative proton-channel designer under aerobic conditions to continuously supply batches of grown designer algal cultures that are subsequently used for enhanced $H_2$ production expression of the proton channels into both the photosynthetic membrane and other cellular membranes such as the mitochondrial membranes under anaerobic conditions. After the non-regenerative proton-channel designer algal cultures are used for enhanced $H_2$ production under anaerobic conditions, they are quite safely handled as non-living biomass materials for disposal including possible use as a fertilizer or other biomass processes.

With a thylakoid-targeted mechanism that enables insertion of the polypeptide proton channels only into the thylakoid membrane so that all of the other cellular functions (including functions of the mitochondria, nucleus, and cell membranes) are kept intact, the result can be much better for certain applications. After the thylakoid-targeted insertion of proton channels, the cell will not only be able to produce $H_2$ but also to grow and regenerate itself when it is returned to aerobic conditions. Our daily experience with photoheterotrophically grown photosynthetic mutants of algae with acetate-containing culture media has demonstrated that this type of designer alga, which contains normal mitochondria, should be able to use the reducing power (NADH) from organic reserves (and/or some exogenous organic substrate such as acetate) to power the cell immediately after its return to aerobic conditions. Consequently, when the alga is returned to aerobic conditions after its use under anaerobic conditions for photoevolution of $H_2$ and $O_2$, the cell will stop making the polypeptide proton channels and start to restore its normal photoautotrophic capability by synthesizing new and functional thylakoids. Consequently, it is also possible to use this genetically transformed organism for repeated cycles of photoautotrophic growth under normal aerobic conditions and efficient production of $H_2$ and $O_2$ by photosynthetic water splitting under anaerobic conditions.

Targeted insertion of designer proton channel is accomplished through the use of a specific targeting DNA sequence 306 that is located between the promoter 304 and the designer proton-channel DNA as shown in the DNA construct 300. In various embodiments, there are a number of transit peptide sequences that can be selected and/or modified for use as the targeting sequence 306 for the targeted insertion of the designer proton channels into algal photosynthetic membrane and, when desirable, other cellular membranes, such as mitochondrial membrane. The targeting sequences 306 that can be used and/or modified for this purpose include (but are not limited to) the transit-peptide sequences of: plastocyanin apoprotein (Pcy1), the LhcII apoproteins, OEE1 apoprotein (PsbO), OEE2 apoprotein (PsbP), OEE3 apoprotein (PsbQ), hydrogenase apoproteins (such as Hyd1), PSII-T apoprotein (PsbT), PSII-S apoprotein (PsbS), PSII-W apoprotein (PsbW), $CF_oCF_1$ subunit-γ apoprotein (AtpC), $CF_oCF_1$ subunit-δ apoprotein (AtpD), $CF_oCF_1$ subunit-II apoprotein (AtpG), photosystem I (PSI) apoproteins (such as, of genes PsaD, PsaE, PsaF, PsaG, PasH, and PsaK), Rubisco SSU apoproteins (such as RbcS2), α-tubulin (TubA), β-tubulin (TubB2), mitochondrial carbonic anhydrase apoproteins (Ca1 and Ca2), mitochondrial transit-peptide sequences of nuclear genes, chloroplast transit-peptide sequences of nuclear genes, and/or their analogs and modified designer sequences.

The following are examples of transit peptide sequences that could be chosen to guide the genetic insertion of the designer proton channels into algal thylakoid membrane: (1)

The transit peptide from the plastocyanin gene targets the lumen of the thylakoids from which the biochemical properties of the designer proton-channel polypeptide may again generate insertion into the thylakoid membrane; (2) The Hyd1 transit peptide confers importation of polypeptides into the stroma, from which the biochemical properties of the designer proton-channel protein may generate insertion into the thylakoid; (3) The transit peptides from the recently characterized Lhcb gene family members lead the LhcII apoproteins directly to the thylakoid and may also do so for the designer proton-channel polypeptide in an artificial construct; and (4) The transit peptide from the Cyc6 gene targets the lumen of the thylakoids from which the biochemical properties of the designer proton-channel polypeptide may again generate insertion into the thylakoid.

Figure 3:
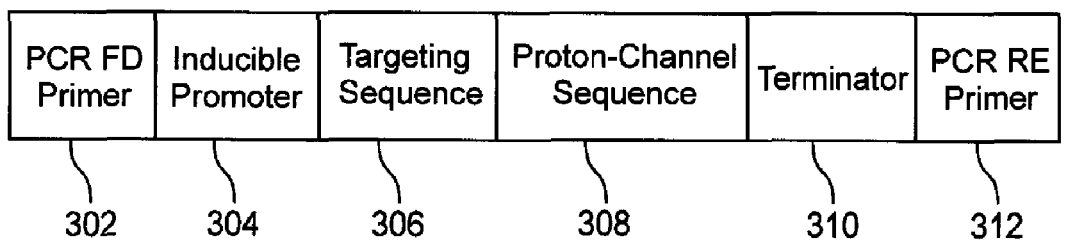
FIG. 3 illustrates one embodiment of the general design of the DNA construct for a designer proton-channel gene.

As illustrated in FIG. 3, in one embodiment the designer DNA construct 300 also contains a terminator 310 after the proton-channel encoding sequence 308 and a pair of polymerase chain reaction (PCR) primers 302, 312 located each at the two ends of the DNA construct 300. The terminator DNA sequence 310, which is designed based on the sequences of natural gene terminators, is to ensure that the transcription and translation of the said designer proton-channel gene are properly terminated to produce an exact designer proton-channel protein as desired.

The two PCR primers 302, 312 are a PCR forward primer (PCR FD primer) 302 located at the beginning (the 3' end) of the DNA construct 300 and a PCR reverse primer (PCR RE primer) 312 located at the other end as shown in FIG. 3. This pair of PCR primers 302, 312 is designed to provide certain convenience when needed for relatively easy PCR amplification of the designer DNA construct 300, which is helpful not only during and after the designer DNA construct 300 is synthesized in preparation for gene transformation, but also after the designer DNA construct 300 is delivered into the genome of a host alga for verification of the designer proton-channel gene in the transformants. For example, after the transformation of the designer gene is accomplished in a *Chlamydomonas reinhardtii*-arg7 host cell using the techniques of electroporation and argininosuccinate lyase (arg7) complementation screening, the resulted transformants can be then analyzed by a PCR DNA assay of their nuclear DNA using this pair of PCR primers 302, 312 to verify whether the entire designer proton-channel gene (the DNA construct 300) is successfully incorporated into the genome of a given transformant. When the nuclear DNA PCR assay of a transformant can generate a PCR product that matches with the predicted DNA size and sequence according to the designer DNA construct 300, the successful incorporation of the designer proton-channel gene into the genome of the transformant is verified.

Therefore, the various embodiments also teach the associated method to effectively create the designer transgenic algae to increase photobiological $H_2$ production efficiency. This method, in one embodiment, includes the following steps: a) Selecting appropriate host algae with respect to their genetic backgrounds and special features in relation to $H_2$ production; b) Genetically deleting any $H_2$-consuming activities such as the uptake-hydrogenase activities in the selected host algae; c) Introducing the nucleic acid constructs of the designer proton-channel genes into the genome of said host algae; d) Verifying the incorporation of the designer proton-channel genes in the transformed algae with DNA PCR assays using the said PCR primers 302, 312 of the designer DNA construct 300; e) Measuring and verifying the designer algae features such as the inducible expression of the designer proton channels for enhanced photosynthetic $H_2$ production from water by assays of mRNA, protein, and $H_2$-production characteristics according to the specific designer features of the DNA construct (FIG. 3).

The above embodiment of the method for creating the designer transgenic algae to increase photobiological $H_2$ production efficiency can also be repeatedly applied for a plurality of operational cycles to achieve more desirable results. In various embodiments, any of the steps a) through e) of this method described above are adjusted to suit for certain specific conditions. In various embodiments, any of the steps a) through e) of the method are applied in full or in part, and/or in any adjusted combination.

In various embodiments, the host organisms for transformation of the designer proton-channel genes to create the transgenic designer photosynthetic organism are selected from the group that includes green algae, brown algae, red algae, blue-green algae, marine algae, freshwater algae, cold-tolerant algal strains, heat-tolerant algal strains, oxygen-tolerant-hydrogenase algal strains, $H_2$-consuming-activity-deleted algal strains, uptake-hydrogenase-deleted algal strains, and combinations thereof. *Chlamydomonas reinhardtii* is a green alga that has had its genome sequenced. Therefore, it is a good model organism, although the technology is applicable to any of the algae mentioned above for enhanced photobiological $H_2$ production. Proper selection of host organisms for their genetic backgrounds and certain special features is also beneficial. For example, the designer proton-channel alga created from a cold-tolerant host strain, such as *Chlamydomonas* cold strain CCMG1619 that has been characterized to produce $H_2$ as cold as 4° C., enables the use even in cold seasons or regions such as Canada. Meanwhile, the designer proton-channel alga created from a thermophilic photosynthetic organism, such as *Synechococcus bigranulatus*, enables the practice to be well extended into the hot seasons or areas such as Mexico and the Southwestern region of the United States, including Nevada, California, Arizona, New Mexico and Texas, where the weather temperature can often be high. Furthermore, the designer proton-channel alga created from a marine alga, such as *Platymonas subcordiformis*, enables using seawater, while the designer alga created from a freshwater alga such as *Chlamydomonas reinhardtii* uses freshwater.

Another feature of various embodiments is that the designer proton-channel algae are devoid of any $H_2$-consuming activity that is not desirable for net $H_2$ production. That is, the designer proton-channel algae will not consume any $H_2$ that it can produce. This feature, which further enhances the net efficiency for photobiological $H_2$ production, is incorporated by genetic inactivation or deletion of the $H_2$-consuming activity. The uptake hydrogenase activity is generally responsible for the $H_2$-consuming activity in algae. Therefore, this additional feature is incorporated by creating the designer algae from a host alga that has its uptake hydrogenase activity genetically deleted. Additional optional features of the designer proton-channel alga include the benefits of reduced chlorophyll-antenna size which has been demonstrated to provide higher photosynthetic productivity and $O_2$-tolerant hydrogenase like the [NiFe] hydrogenases of *Ralstonia eutropha* which can function under aerobic conditions. In various embodiments, these optional features are incorporated into the designer alga also by use of an $O_2$-tolerant hydrogenase and/or chlorophyll antenna-deficient mutant (e.g., *Chlamydomonas reinhardtii* DS521) as a host organism for gene transformation with the designer proton-channel DNA constructs 300.

Examples of the designer proton-channel genes (DNA constructs) are shown in the sequence listings. SEQ ID NO: 1 presents a detailed DNA construct of a designer proton-channel gene that includes a PCR FD primer (1-20), a 458-bp HydA1 promoter (21-478), a Plastocyanin transit-peptide DNA sequence (479-618), a Melittin DNA sequence (619-703), an RbcS2 terminator (704-926), and a PCR RE primer (927-945). This DNA construct (example 1) has been delivered into the nuclear genome of a *Chlamydomonas reinhardtii*-arg7 host cell using the techniques of electroporation and argininosuccinate lyase (arg7) complementation screening to create the proton-channel designer alga. The 458-bp HydA1 promoter (DNA sequence 21-478) is used as an example of an inducible promoter to control the expression of a Melittin proton channel (DNA sequence 619-703). The RbcS2 terminator (DNA sequence 704-926) is employed to ensure that the transcription and translation of the proton-channel gene is properly terminated to produce the exact designer proton-channel protein (Melittin) as desired. Because the HydA1 promoter is a nuclear DNA that can control the expression only for nuclear genes, the synthetic proton-channel gene in this example is designed according to the codon usage of *Chlamydomonas* nuclear genome. Therefore, in this case, the designer proton-channel gene is transcribed in nucleus. Its mRNA is naturally translocated into cytosol, where the mRNA is translated to an apoprotein that consists of the Melittin protein (corresponding to DNA sequence 619-703) and the Plastocyanin transit peptide (corresponding to DNA sequence 479-618) linked together. The transit peptide of the apoprotein guide its transportation across the chloroplast membranes and into the thylakoids, where the transit peptide is cut off from the apoprotein and the resulting free melittin (polypeptide proton channel) insert itself into the thylakoid membrane from the lumen side. The action of the designer proton channel in the thylakoid membranes then provides the benefit of simultaneously eliminating the four proton-gradient gradient related problems in relation to photobiological H2 production. The two PCR primers (sequences 1-20 and 927-945) are selected from the sequence of a Human actin gene and can be paired with each other. Blasting the sequences against *Chlamydomonas* GenBank found no homologous sequences of them. Therefore, they can be used as appropriate PCR primers in DNA PCR assays for verification of the designer proton-channel gene in the transformed alga.

SEQ ID NO: 2 presents example 2 of a designer proton-channel DNA construct that includes a PCR FD primer (sequence 1-20), a 282-bp HydA1 promoter (21-302), a Xho I NdeI site (303-311), a Plastocyanin transit peptide sequence (312-452), a Melittin proton channel (453-536), a XbaI site (537-545), a RbcS2 terminator (546-768), and a PCR RE primer (769-787). This designer proton channel gene (example 2) is quite similar to example 1, SEQ ID NO: 1, except that a shorter promoter sequence is used and restriction sites of Xho I NdeI and XbaI are added to make the key components such as the targeting sequence (312-452) and proton channel (453-536) as a modular unit that can be flexible replaced when necessary to save cost of gene synthesis and enhance work productivity. Please note, the proton channel does not have to be a Melittin; a number of other proton-channel structures such as a gramicidin analog channel can also be used. This designer proton-channel gene (SEQ ID NO: 2) has also been successfully delivered into the nuclear genome of a *Chlamydomonas reinhardtii*-arg7 host cell using the techniques of electroporation and argininosuccinate lyase (arg7) complementation screening to create the proton-channel designer alga.

SEQ ID NO: 3 presents example 3 of a designer proton-channel DNA construct that includes a PCR FD primer (1-20), a 458-bp HydA1 promoter (21-478), a HydA1 transit peptide (479-646), a Melittin (647-730), an RbcS2 terminator (731-953), and a PCR RE primer (954-972). This designer proton-channel gene (example 3) is also similar to example 1, with the exception that a HydA1 transit peptide sequence (479-646) is used here so that the proton channel protein is synthesized in the cytosol, delivered into the chloroplast, and inserted into the thylakoid membrane from the stoma side. This designer proton-channel gene (SEQ ID NO: 3) has also been successfully delivered into the nuclear genome of an algal host cell to create the proton-channel designer alga.

Figure 5:
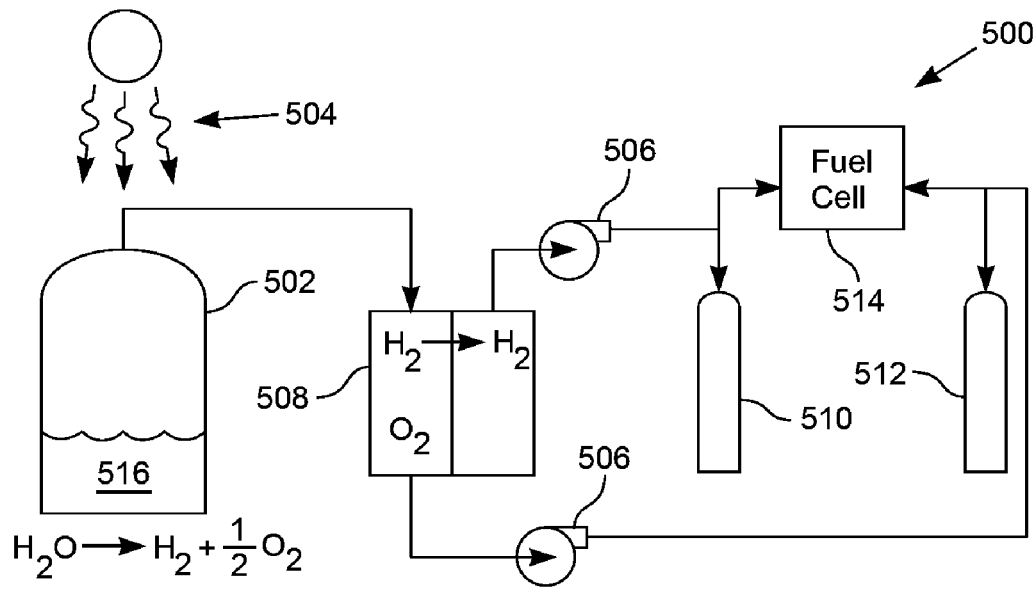
FIG. 5 illustrates the designer proton-channel algae in one embodiment of an algal reactor and gas-separation-utilization system.
Figure 6:
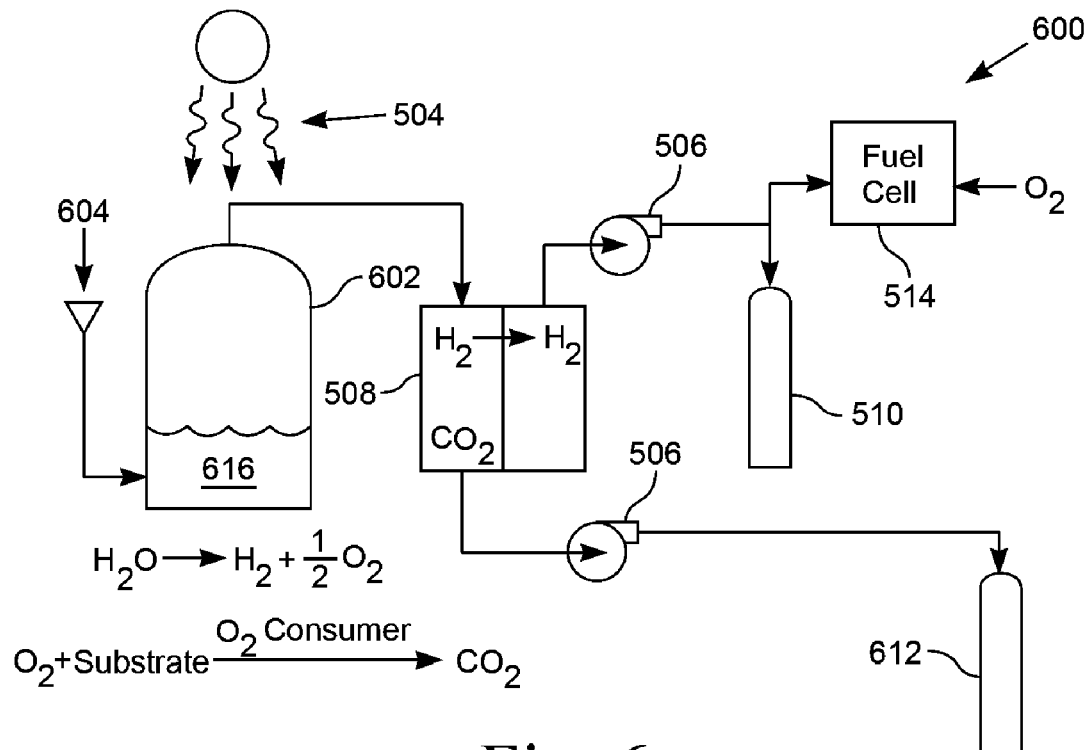
FIG. 6 illustrates the designer proton-channel algae with $O_2$-consuming microbes in one embodiment of a photo-bioreactor and gas-separation-utilization system.

Another embodiment teaches how the designer proton-channel alga is used with bioreactor systems 500, 600 for efficient photobiological $H_2$ production (FIGS. 5 and 6). As explained previously, one embodiment of the proton-channel designer algae, such as the one that contains a hydrogenase-promoter-controlled designer proton-channel gene, grows normally under aerobic conditions (FIG. 4A) by autotrophic photosynthesis using air $CO_2$ in a manner similar to that of a wild-type organism (FIG. 1).

In one embodiment, to receive the maximal benefit by fully using the potential capabilities of the inducible proton-channel designer algae, it is a preferred practice to grow the designer algae photoautotrophically using air $CO_2$ as the carbon source under the aerobic conditions in a minimal medium that contain the essential mineral (inorganic) nutrients. No organic substrate such as acetate is required to grow the designer algae under the normal conditions before the designer proton-channel gene is expressed. Most of the algae grows rapidly in water through autotrophic photosynthesis using air $CO_2$ as long as there are sufficient mineral nutrients. The nutrient elements that are commonly required for algal growth are: N, P, and K at the concentrations of about 1-10 mM, and Mg, Ca, S, and Cl at the concentrations of about 0.5 to 1.0 mM plus some trace elements Mn, Fe, Cu, Zn, B, Co, Mo and etc at µM concentration levels. All of the mineral nutrients are supplied in an aqueous minimal medium that is made with well-established recipes of algal culture media using some water and relatively small amounts of inexpensive fertilizers and mineral salts, such as ammonium bicarbonate ($NH_4HCO_3$) [or ammonium nitrate, urea, ammonium chloride], potassium phosphates ($K_2HPO_4$ and $KH_2PO_4$), magnesium sulfate heptahydrate ($MgSO_4.7H_2O$), calcium chloride ($CaCl_2$), zinc sulfate heptahydrate ($ZnSO_4.7H_2O$), iron (II) sulfate heptahydrate ($FeSO_4.7H_2O$), and boric acid ($H_3BO_3$) etc. That is, large amounts of designer algae cells (biocatalysts) can be inexpensively grown in a short period of time because, under aerobic conditions such as in an open pond, the designer algae photoautotrophically grow by themselves using air $CO_2$ as rapidly as their wild-type parental strains. This is a feature (benefit) that provides a cost-effective solution in generation of photoactive biocatalysts (the designer proton-channel algae) that are alternative to the silicone-photovoltaic-based technologies for renewable solar energy production.

When the algal culture is grow and ready for $H_2$ production, the grown algal culture is sealed or placed into certain specific conditions, such as anaerobic conditions that can be generated by removal of $O_2$ from the sealed algal reactor, to induce the expression of designer proton channels. When the designer proton-channel gene is expressed simultaneously with the induction of the hydrogenase enzyme under anaerobic conditions that can be achieved by removal of $O_2$ from the culture, the algal cells are essentially turned into efficient and robust "green machines" that are perfect for photoevolution of $H_2$ and $O_2$ by water splitting (FIG. 4B). Production of $H_2$ and $O_2$ by direct photosynthetic water splitting can, in principle, have high quantum yield. Theoretically, it requires only 4 photons to produce a $H_2$ molecule and $\frac{1}{2}O_2$ from water by this mechanism. The maximal theoretical sunlight-to-$H_2$ energy efficiency by the process of direct photosynthetic water-splitting is about 10%, which is the highest possible among all the biological approaches. Application of the designer proton-channel algae maximally realizes the potential of this photosynthetic water-splitting process for $H_2$ production because all the four proton-gradient related physiological problems (illustrated in FIG. 1) that limit the rate of photobiological $H_2$ production from water are eliminated by use of the designer alga (FIGS. 4A and 4B). Consequently, this approach has great potential when implemented properly with an algal $H_2$-production reactor and a gas-separation/utilization system 500 (illustrated in FIG. 5).

FIG. 5 illustrates one embodiment of an algal reactor and gas-separation-utilization system 500 for simultaneous photosynthetic production of $H_2$ and $O_2$ from water ($H_2O$) with effective harvesting and utilization of the gas products including (but not limited to) fuel-cell application for electricity generation. An algal reactor 502 contains a quantity of the designer alga 516 that is exposed to light 504, such as sunlight. The $H_2$ and $O_2$ produced in the algal reactor 502 are pulled through a $H_2$ separation membrane 508 by vacuum pumps 506. The $O_2$ on one side of the membrane 508 is transferred to an $O_2$ storage tank 512 and a fuel cell 514. The $H_2$ on the opposite side of the membrane 508 is transferred to an $H_2$ storage tank 510 and the fuel cell 514. Those skilled in the art will recognize that other configurations of a system 500 can be implemented without departing from the spirit and scope of the present invention.

Therefore, this embodiment of using the designer algae for photosynthetic $H_2$ and $O_2$ production from water with algal reactor and a gas-separation/utilization system 500 includes a specific process described as a series of the following steps: a) Growing a designer transgenic alga photoautotrophically in minimal culture medium using air $CO_2$ as the carbon source under aerobic (normal) conditions before inducing the expression of the designer proton channel; b) When the algal culture is grown and ready for $H_2$ production, sealing or placing the algal culture into a specific condition, such as an anaerobic condition that can be generated by removal of $O_2$ from the algal reactor 502, to induce the expression of designer proton channels; c) When the designer proton channels are expressed and inserted into the algal photosynthetic membranes, supplying visible light energy 504, such as sunlight, for the proton-channel-expressed designer algal cells to work as the catalysts for photosynthetic production of $H_2$ and $O_2$ from water; d) Harvesting the $H_2$ and $O_2$ gas products immediately and continuously from the algal reactor 502 by a combination of vacuum pumps 506, separation of the gas products through a nanometer ($H_2$ separating) membrane 508, and coupled utilization and/or storage of the $H_2$ and $O_2$ gas products with fuel-cell 514 operation for electricity generation and/or with a $H_2$ storage tank 510 and/or a $O_2$ storage tank 512 and/or specific $H_2$- or $O_2$-absorbing materials including metal hydrides; e) Strictly keeping the concentrations of $H_2$ and $O_2$ in the algal reactor 502 always low enough to ensure safety for continuing photobiological $H_2$ production through the designer-alga photosynthetic water-splitting process; and f) harvesting the used transgenic algal biomass.

The process illustrated in FIG. 5 with the algal reactor and a gas-separation/utilization system 500 can, certainly, be repeated for a plurality of operational cycles to achieve desirable results. In various embodiments, any of the steps a) through f) of this process described above are adjusted to suit for certain specific conditions. In practice, any of the steps a) through f) of the process are applied in full or in part, and/or in any adjusted combination as well.

It is worthwhile to note that the removal of $O_2$ from algal culture can be achieved by a number of techniques, such as the use of a vacuum pump 506 after the grown algal culture 516 is sealed from atmospheric air $O_2$. Because the production of $H_2$ and $O_2$ by direct photosynthetic water occurs in the same bioreactor volume, an effective gas-products separation process, such as the nanometer membrane 508 technology shown in FIG. 5 for effective separation of $H_2$ and $O_2$ from the gas mixture, is necessary. Furthermore, consideration must be taken for safe handling of the $H_2$ and $O_2$ mixture, which is potentially explosive in case that the concentration of gas mixture reaches the explosion limits. Innovative application of a vacuo-photosynthetic reactor and gas-separation system also helps address the safety issue by strictly maintaining the concentration of $H_2$ and $O_2$ well below the explosion limits by effectively removing the gas products from the bioreactor system. In one embodiment, use of a fuel cell 514 that effectively consumes $H_2$ and $O_2$ for electricity generation also helps to remove the gas products from the bioreactor and gas-separation system 500. In other embodiments, use of certain hydrogen storage materials, such as metal hydrides that can effectively adsorb $H_2$, also helps to remove the $H_2$ gas product from the bioreactor and gas-separation system 500. Certain engineering technology, such as use of argon or hydrofluorocarbon gas as an inert retardant in the bioreactor and gas-separation system 500, also improves the safe handling of the $H_2$ and $O_2$ mixture.

The various embodiments teach yet another approach to avoid the $O_2$-related problems in using the designer algae by adding certain $O_2$-consuming microbes and organic substrates 604 into the algal photo-bioreactor system 600 illustrated in FIG. 6. FIG. 6 illustrates one embodiment of a photo-bioreactor and gas-separation-utilization system 600 for simultaneous production of $H_2$ and $CO_2$ through combination of photosynthetic water splitting by the designer proton-channel algae and respiratory consumption of the $O_2$ molecules primarily by $O_2$-consuming microbes using organic substrate 604. A photo-bioreactor 602 contains a quantity of the designer alga 616 that is exposed to light 504, such as sunlight. The $H_2$ and $CO_2$ produced in the photo-bioreactor 602 are pulled through a $H_2$ separation membrane 508 by vacuum pumps 506. The $CO_2$ on one side of the membrane 508 is transferred to a $CO_2$ storage tank 612. The $H_2$ on the opposite side of the membrane 508 is transferred to a $H_2$ storage tank 510 and a fuel cell 514, which also uses atmospheric $O_2$. Organic substrate 604 is added to the designer alga 616 in the photo-bioreactor 602. Those skilled in the art will recognize that other configurations of a system 600 can be implemented without departing from the spirit and scope of the present invention.

The embodiment of the system 600 illustrated in FIG. 6 uses the designer algae with $O_2$-consuming microbes 616 to produce $H_2$ and $CO_2$ from $H_2O$ and organic substrates with a photo-bioreactor 602 and gas-product separation and utilization system 600 (illustrated in FIG. 6). The embodiment includes a process including the following steps: a) Growing a designer transgenic alga photoautotrophically in minimal culture medium using air $CO_2$ as the carbon source and/or photoheterotrophically using organic substrate under aerobic conditions; b) Sealing the grown algal culture from atmospheric air oxygen to start creating anaerobic conditions in the photo-bioreactor 602; c) Introducing $O_2$-consuming microbes and adding organic substrate 604 into said photo-bioreactor 602 to consume any residual $O_2$ and maintain the anaerobic conditions in the bioreactor 602; d) Allowing a certain period of time, for example, about 2-12 hours, for the $O_2$-consuming microbes and the algal cells to fully consume any residual $O_2$ in the sealed bioreactor 602 by their oxidative respiratory activities to generate anaerobic conditions to express the designer proton channels into algal photosynthetic membranes along with induction of the hydrogenase; e) When the designer proton channels are expressed and inserted into algal photosynthetic membranes, supplying visible light energy 504, such as sunlight, for the proton-channel-expressed designer algal cells as the catalysts to photosynthetically produce $H_2$ and $O_2$ from water while the oxidative respiratory activities of the $O_2$-consuming microbes (and the algal cells) consuming the produced $O_2$ molecules with production of $CO_2$ using organic substrates; f) Monitoring and maintaining proper balance between the photosynthetic $H_2$ and $O_2$ production process and the $O_2$ consuming activity with the option of sufficient and continuous supply of organic substrates so that the net gas-products are nearly pure $H_2$ and $CO_2$. g) Harvesting the $H_2$ and $CO_2$ gas products from the photo-bioreactor 602 by a combination of vacuum pumps 506, separation of the gas products through a nanometer ($H_2$ separation) membrane 508, and coupled utilization of the $H_2$ and $CO_2$ gas products by fuel-cell 514 operation for electricity generation and/or storage of the gas products by using of storage tanks 510, 612 and/or specific $H_2$-absorbing materials including metal hydrides; h) Strictly keeping the concentration of $O_2$ in the sealed photo-bioreactor system 600 low enough to ensure safety and continued photobiological production of $H_2$ and $CO_2$ from water and organic substrates; and i) harvesting the used transgenic algal and microbial biomass.

In the process illustrated in FIG. 6, the photo-bioreactor and gas-product separation and utilization system 600 can, of course, be repeatedly operated for a plurality of cycles to achieve desirable results. In various embodiments, any of the steps a) through i) of the process described above are adjusted to suit for certain specific conditions. In practice, any of the steps a) through i) of the process (FIG. 6) are applied in full or in part, or in any adjusted combination as well.

Examples of suitable $O_2$-consuming microbes are uptake-hydrogenases-deleted facultative bacteria, $H_2$-producing facultative bacteria, and/or $H_2$-producing facultative photosynthetic bacteria that can consume $O_2$ (but not $H_2$) using organic substrates to maintain the bioreactor medium under anaerobic conditions favoring production of $H_2$. Examples of usable substrates 604 are organic acids, acetate, ethanol, sugars, carbohydrates, lipids, proteins, methanol, propanol, butanol, acetone, and biomass materials.

In the process illustrated in FIG. 6, the designer proton-channel algae efficiently produce $H_2$ and $O_2$ by photosynthetic water splitting as before according to the following process reaction:

$$2H_2O \rightarrow 2H_2 + O_2 \qquad (1)$$

The $O_2$-consuming microbes such as the uptake-hydrogenases-deleted facultative $H_2$-producing bacteria then use organic substrates to effectively consume the $O_2$ molecules that are generated by the alga according to the following process reaction:

$$O_2 + \text{organic substrate} \rightarrow mCO_2 + nH_2 \qquad (2)$$

The consumption of $O_2$ molecules by the $O_2$-consuming microbes keeps the bioreactor medium under the anaerobic conditions that favor the continued $H_2$ production. The net result from the combination of the two process reactions (1 and 2) is the conversion of water ($H_2O$) and organic substrate to hydrogen ($H_2$) and carbon dioxide ($CO_2$). Since the gas product from the system 600 illustrated in FIG. 6 is essentially pure $H_2$ and $CO_2$ without $O_2$, the problems of $H_2$ and $O_2$ mixture (which represent the following three $O_2$-related technical problems: the drainage of electrons by $O_2$, the poisoning of the hydrogenase enzyme by $O_2$, and the gas-separation and safety issues) are now avoided. In various embodiments, gas production separation of $H_2$ from $CO_2$ is readily accomplished with technologies such as nanometer membranes and pressure-swing gas-separation technologies. The $H_2$ gas produced by system 600 can also be used for cash sales and/or for onsite fuel-cell operation to generate electricity (FIG. 6).

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. A transgenic alga comprising at least one exogenous transgene encoding a proton conductive polypeptide in a photosynthetic membrane of the transgenic alga, wherein the proton conductive polypeptide is a polynucleotide sequence for a designer proton-conductive polypeptide, and wherein the designer proton-conductive polypeptide comprises SEQ ID NO: 1.

2. A transgenic alga comprising at least one exogenous transgene encoding a proton conductive polypeptide in a photosynthetic membrane of the transgenic alga, wherein the proton conductive polypeptide is a polynucleotide sequence for a designer proton-conductive polypeptide, and wherein the designer proton-conductive polypeptide comprises SEQ ID NO: 2.

3. A transgenic alga comprising at least one exogenous transgene encoding a proton conductive polypeptide in a photosynthetic membrane of the transgenic alga, wherein the proton conductive polypeptide is a polynucleotide sequence for a designer proton-conductive polypeptide, and wherein the designer proton-conductive polypeptide comprises SEQ ID NO: 3.

* * * * *